US012706176B1

(12) United States Patent
Pardhe et al.

(10) Patent No.: US 12,706,176 B1
(45) Date of Patent: Aug. 11, 2026

(54) METHODS, SYSTEMS, AND COMPUTER READABLE MEDIA FOR GENERATING CODON OPTIMIZED NUCLEOTIDE SEQUENCES

(71) Applicant: ARIZONA BOARD OF REGENTS ON BEHALF OF ARIZONA STATE UNIVERSITY, Scottsdale, AZ (US)

(72) Inventors: Mary Pardhe, Phoenix, AZ (US); Hugh Mason, Phoenix, AZ (US); Tsafrir S Leket-Mor, Tempe, AZ (US); Joshua Pardhe, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1386 days.

(21) Appl. No.: 17/401,440

(22) Filed: Aug. 13, 2021

Related U.S. Application Data

(60) Provisional application No. 63/065,252, filed on Aug. 13, 2020.

(51) Int. Cl.
*G16B 30/20* (2019.01)
*C12P 21/00* (2006.01)

(52) U.S. Cl.
CPC .............. *G16B 30/20* (2019.02); *C12P 21/00* (2013.01)

(58) Field of Classification Search
CPC ........ G16B 30/00; G16B 30/10; G16B 30/20; G16B 35/00; G16C 20/60; C12P 21/00
See application file for complete search history.

(56) References Cited

U.S. PATENT DOCUMENTS

2004/0005600 A1 1/2004 Angov et al.
2013/0123483 A1 5/2013 Raab et al.
2019/0325989 A1* 10/2019 Lipowsky .............. G16B 40/00

OTHER PUBLICATIONS

Puigbo, Pere, et al. "OPTIMIZER: a web server for optimizing the codon usage of DNA sequences." Nucleic acids research 35. suppl_2 (2007): W126-W131. (Year: 2007).*

Mauro, Vincent P., and Stephen A. Chappell. "A critical analysis of codon optimization in human therapeutics." Trends in molecular medicine 20.11 (2014): 604-613. (Year: 2014).*

Goli, B., & S Nair, A. (2012). The Elusive Short Gene—an ensemble method for recognition for prokaryotic genome. Biochemical and Biophysical Research Communications, 422(1), 36-41. https://doi.org/10.1016/j.bbrc.2012.04.090. (Year: 2012).*

Ohtsuka E, Ikehara M, Sã¶|| D. Recent developments in the chemical synthesis of polynucleotides. Nucleic Acids Res. 1982;10(21): 6553-6570. (Year: 1982).*

Hershberg, Ruth, and Dmitri A. Petrov. "General rules for optimal codon choice." PLoS genetics 5.7 (2009): e1000556. (Year: 2009).*

Fuglsang, Anders. "Codon optimizer: a freeware tool for codon optimization." Protein expression and purification 31.2 (2003): 247-249. (Year: 2003).*

* cited by examiner

*Primary Examiner* — Olivia M. Wise
*Assistant Examiner* — Keenan Neil Anderson-Fears
(74) *Attorney, Agent, or Firm* — MHZ Technology Law Group LLP

(57) ABSTRACT

Provided herein are methods of generating codon optimized nucleotide sequences. The methods include reverse-translating a target amino acid sequence multiple times to generate a plurality of candidate codon optimized nucleotide sequences in which a given codon is randomly selected from synonymous codons encoding a given amino acid residue and incorporated into a given candidate codon optimized nucleotide sequence in the plurality of candidate codon optimized nucleotide sequences. The methods also include determining a total number of occurrences of problematic nucleotide sequences in each of the candidate codon optimized nucleotide sequences to generate a problematic nucleotide sequence count for each of the candidate codon optimized nucleotide sequences. In addition, the methods also include identifying candidate codon optimized nucleotide sequences that comprise a lowest problematic nucleotide sequence count. Additional methods as well as related systems and computer readable media are also provided.

13 Claims, 5 Drawing Sheets

METHODS, SYSTEMS, AND COMPUTER READABLE MEDIA FOR GENERATING CODON OPTIMIZED NUCLEOTIDE SEQUENCES

CROSS-REFERENCE TO RELATED APPLICATIONS

This application claims priority to U.S. Provisional Patent Application Ser. No. 63/065,252, filed Aug. 13, 2020, the disclosure of which is incorporated herein by reference.

BACKGROUND

Many pharmaceutically or industrially relevant proteins are produced using heterologous expression systems, including bacterial, fungal, and mammalian cells, among other such systems. Heterologous expression often involves the introduction of DNA (e.g., cDNA) or RNA encoding the protein of interest or target protein from one species into the cell of another species, which acts as the host for the expression of the target protein. The genetic code universally assigns specific sets of three consecutive nucleotides (codons) to each of the 20 "standard" amino acids and three translation stop signals. The genetic code is referred to as "degenerate" because there are 64 potential combinations of three nucleotides, most of the amino acids are encoded by more than one "synonymous" codon. While the near universality of the genetic code allows any given coding sequence to be appropriately translated in any given host cell, organisms often exhibit species-specific bias toward use of subsets of synonymous codons. Accordingly, polynucleotide sequences encoding target proteins are typically altered or "optimized" for expression in the heterologous host organism in view of that organism's codon usage or preference. In addition, such polynucleotide sequences are also generally optimized to account for problematic nucleotide sequences that may otherwise inhibit the target protein's expression in the host organism. Examples of such problematic nucleotide sequences, include guanine-cytosine content (GC content), sequence repeats, and other sequence motifs (e.g., splice sites, restriction enzyme recognition sites, etc.) that may negatively affect transcription and/or translation in a given host expression system.

The various optimization demands can be, and most often are, in conflict with each other, requiring an elaborate multi-step, reiterative and hierarchical decision-making process ripe for automation via computational algorithms. Accordingly, there is a need for additional methods, and related aspects, of generating codon optimized nucleotide sequences for expression in heterologous host systems that account for differing codon usage and problematic nucleotide sequences.

SUMMARY

The present disclosure relates, in certain aspects, to methods of generating codon optimized nucleotide sequences for optimized expression of encoded polypeptide sequences in host expression systems. To permit computationally feasible sequence optimization, aspects of brute force and/or find-and-replace methods are implemented in some embodiments. In other exemplary embodiments, concatenation-based methods are used. In addition, the methods of the present disclosure also allow for user customization, including user selected or defined codon weightings. These and other aspects will be apparent upon a complete review of the present disclosure, including the accompanying figures.

In one aspect, the present disclosure provides a method of generating a codon optimized nucleotide sequence using a computer. The method includes receiving, by the computer, a target amino acid sequence, at least one problematic nucleotide sequence, and a selected host expression system and/or a selected codon table (e.g., a user specified codon table). In some embodiments, the selected codon table is automatically received when the selected host expression system is received by the computer. In some embodiments, the target amino acid sequence corresponds to at least one protein (e.g., a therapeutic protein, a prophylactic protein, etc.). Typically, the host expression system comprises a viral species, a fungal species, a bacterial species, a mammalian species, or the like. The method also includes reverse-translating, by the computer, the target amino acid sequence multiple times to generate a plurality of candidate codon optimized nucleotide sequences that each encode the target amino acid sequence, wherein for an amino acid residue in the target amino acid sequence that is encoded by synonymous codons, a given codon is randomly selected from the synonymous codons encoding the amino acid residue and incorporated into a given candidate codon optimized nucleotide sequence in the plurality of candidate codon optimized nucleotide sequences. The method also includes determining, by the computer, a total number of occurrences of the problematic nucleotide sequence in each of the candidate codon optimized nucleotide sequences in the plurality of candidate codon optimized nucleotide sequences to generate a problematic nucleotide sequence count for each of the candidate codon optimized nucleotide sequences. In addition, the method also includes identifying, by the computer, one or more of the candidate codon optimized nucleotide sequences in the plurality of candidate codon optimized nucleotide sequences that comprise a lowest problematic nucleotide sequence count, thereby generating the codon optimized nucleotide sequence.

In another aspect, the present disclosure provides a method of generating a codon optimized nucleotide sequence using a computer. The method includes receiving, by the computer, a selected host expression system, a target nucleotide sequence, a selected codon usage frequency, at least one problematic nucleotide sequence, and a selected guanine-cytosine (GC) content percentage, and concatenating, by the computer, two or more selected coding nucleotide sequences from the selected host expression system to generate a concatenated coding nucleotide sequence. The method also includes splitting, by the computer, the concatenated coding nucleotide sequence into codons to generate a set of concatenated coding nucleotide sequence codons, determining, by the computer, w values for synonymous codons in the set of concatenated coding nucleotide sequence codons to generate a set of concatenated coding nucleotide sequence w values, and splitting, by the computer, the target nucleotide sequence into codons to generate a set of target nucleotide sequence codons. In addition, the method also includes determining, by the computer, w values for synonymous codons in the set of target nucleotide sequence codons, a codon adaption index (CAI) for the target nucleotide sequence, and a number of unfavorable codons in the target nucleotide sequence using the set of concatenated coding nucleotide sequence w values to generate target nucleotide sequence baseline data, and modifying, by the computer, the target nucleotide sequence using the target nucleotide sequence baseline data while maintaining the selected codon usage frequency and the selected GC content percentage in the target nucleotide sequence and while minimizing occurrences of the problematic nucleotide sequence in the target nucleotide sequence, thereby generating the codon optimized nucleotide sequence.

In some embodiments, the method further includes determining, by the computer, a total number of codons, a number of unfavorable codons, a CAI, and/or a number of occurrences of the problematic nucleotide sequence in the codon optimized nucleotide sequence. In some embodiments, the method includes determining, by the computer, a geometric mean of w values of the target nucleotide sequence and/or the codon optimized nucleotide sequence.

In some embodiments, the at least one problematic nucleotide sequence comprises at least 2, 3, 4, 5, 6, 7, 8, 9, 10, 11, 12, 13, 14, 15, 16, 17, 18, 19, 20, 30, 40, 50, 100, 500, or more problematic nucleotide sequences. In some embodiments, the at least one problematic nucleotide sequence corresponds to a splice site or a restriction enzyme recognition site.

In some embodiments, the plurality of candidate codon optimized nucleotide sequences comprises at least 100, 1000, 10000, 100000, or more nucleotide sequences. In some embodiments, a given candidate codon optimized nucleotide sequence in the plurality of candidate codon optimized nucleotide sequences comprises about 250 or fewer codons. In some embodiments, the synonymous codons each comprise a corresponding weight. In some embodiments, the corresponding weight is user specified.

In some embodiments, the method further comprises replacing, by the computer, at least sub-sequences of any occurrences of the problematic nucleotide sequence in the codon optimized nucleotide sequence with unproblematic nucleotide sequences that do not alter the encoded target amino acid sequence to generate a further codon optimized nucleotide sequence. In some embodiments, the codon optimized nucleotide sequence comprises about 250 or more codons. In some embodiments, the method includes identifying, by the computer, a start position of the problematic nucleotide sequence, a length of the problematic nucleotide sequence, and/or a number of problematic codons in the problematic nucleotide sequence at each occurrence of the problematic nucleotide sequence in the codon optimized nucleotide sequence to generate problematic nucleotide sequence data. In these embodiments, the method also includes replacing, by the computer, at least the sub-sequences of any occurrences of the problematic nucleotide sequence in the codon optimized nucleotide sequence with the unproblematic nucleotide sequence that is randomly selected from a list of weighted unproblematic nucleotide sequences using the problematic nucleotide sequence data.

In some embodiments, the method further includes synthesizing a polynucleotide comprising the codon optimized nucleotide sequence encoding the target amino acid sequence. In some embodiments, the method further includes inserting the synthesized polynucleotide comprising the codon optimized nucleotide sequence encoding the target amino acid sequence into the selected host expression system, expressing a polypeptide that comprises the target amino acid sequence, and purifying the polypeptide.

In other aspects, the present disclosure provides a system that includes at least one controller that comprises, or is capable of accessing, computer readable media comprising non-transitory computer-executable instructions which, when executed by at least one electronic processor, perform at least receiving a target amino acid sequence, at least one problematic nucleotide sequence, and a selected host expression system and/or a selected codon table. The instructions also perform reverse-translating the target amino acid sequence multiple times to generate a plurality of candidate codon optimized nucleotide sequences that each encode the target amino acid sequence, wherein for an amino acid residue in the target amino acid sequence that is encoded by synonymous codons, a given codon is randomly selected from the synonymous codons encoding the amino acid residue and incorporated into a given candidate codon optimized nucleotide sequence in the plurality of candidate codon optimized nucleotide sequences. The instructions also perform determining a total number of occurrences of the problematic nucleotide sequence in each of the candidate codon optimized nucleotide sequences in the plurality of candidate codon optimized nucleotide sequences to generate a problematic nucleotide sequence count for each of the candidate codon optimized nucleotide sequences. In addition, the instructions also perform identifying one or more of the candidate codon optimized nucleotide sequences in the plurality of candidate codon optimized nucleotide sequences that comprise a lowest problematic nucleotide sequence count to thereby generate a codon optimized nucleotide sequence.

In still other aspects, the present disclosure provides a system, comprising at least one controller that comprises, or is capable of accessing, computer readable media comprising non-transitory computer-executable instructions which, when executed by at least one electronic processor, perform at least receiving a selected host expression system, a target nucleotide sequence, a selected codon usage frequency, at least one problematic nucleotide sequence, and a selected guanine-cytosine (GC) content percentage, concatenating two or more selected coding nucleotide sequences from the selected host expression system to generate a concatenated coding nucleotide sequence, and splitting the concatenated coding nucleotide sequence into codons to generate a set of concatenated coding nucleotide sequence codons. The instructions also perform determining w values for synonymous codons in the set of concatenated coding nucleotide sequence codons to generate a set of concatenated coding nucleotide sequence w values, and splitting the target nucleotide sequence into codons to generate a set of target nucleotide sequence codons. The instructions also perform determining w values for synonymous codons in the set of target nucleotide sequence codons, a codon adaption index (CAI) for the target nucleotide sequence, and a number of unfavorable codons in the target nucleotide sequence using the set of concatenated coding nucleotide sequence w values to generate target nucleotide sequence baseline data, and modifying the target nucleotide sequence using the target nucleotide sequence baseline data while maintaining the selected codon usage frequency and the selected GC content percentage in the target nucleotide sequence and while minimizing occurrences of the problematic nucleotide sequence in the target nucleotide sequence to thereby generate a codon optimized nucleotide sequence.

In still other aspects, the present disclosure provides a computer readable media comprising non-transitory computer-executable instructions which, when executed by at least one electronic processor, perform at least receiving a target amino acid sequence, at least one problematic nucleotide sequence, and a selected host expression system and/or a selected codon table. The instructions also perform reverse-translating the target amino acid sequence multiple times to generate a plurality of candidate codon optimized nucleotide sequences that each encode the target amino acid sequence, wherein for an amino acid residue in the target amino acid sequence that is encoded by synonymous codons, a given codon is randomly selected from the synonymous codons encoding the amino acid residue and incorporated into a given candidate codon optimized nucleotide sequence in the plurality of candidate codon optimized nucleotide sequences. The instructions also perform determining a total number of occurrences of the problematic nucleotide sequence in each of the candidate codon optimized nucleotide sequences in the plurality of candidate codon optimized nucleotide sequences to generate a problematic nucleotide sequence count for each of the candidate codon optimized nucleotide sequences. In addition, the instructions also perform identifying one or more of the candidate codon optimized nucleotide sequences in the plurality of candidate codon optimized nucleotide sequences that comprise a lowest problematic nucleotide sequence count to thereby generate a codon optimized nucleotide sequence.

In still other aspects, the present disclosure provides a computer readable media comprising non-transitory computer-executable instructions which, when executed by at least one electronic processor, perform at least receiving a selected host expression system, a target nucleotide sequence, a selected codon usage frequency, at least one problematic nucleotide sequence, and a selected guanine-cytosine (GC) content percentage, concatenating two or more selected coding nucleotide sequences from the selected host expression system to generate a concatenated coding nucleotide sequence, and splitting the concatenated coding nucleotide sequence into codons to generate a set of concatenated coding nucleotide sequence codons. The instructions also perform determining w values for synonymous codons in the set of concatenated coding nucleotide sequence codons to generate a set of concatenated coding nucleotide sequence w values, and splitting the target nucleotide sequence into codons to generate a set of target nucleotide sequence codons. The instructions also perform determining w values for synonymous codons in the set of target nucleotide sequence codons, a codon adaption index (CAI) for the target nucleotide sequence, and a number of unfavorable codons in the target nucleotide sequence using the set of concatenated coding nucleotide sequence w values to generate target nucleotide sequence baseline data, and modifying the target nucleotide sequence using the target nucleotide sequence baseline data while maintaining the selected codon usage frequency and the selected GC content percentage in the target nucleotide sequence and while minimizing occurrences of the problematic nucleotide sequence in the target nucleotide sequence to thereby generate a codon optimized nucleotide sequence.

In some embodiments of the systems and computer readable media disclosed herein, the instructions further perform at least determining, by the computer, a total number of codons, a number of unfavorable codons, a CAI, and/or a number of occurrences of the problematic nucleotide sequence in the codon optimized nucleotide sequence. In some embodiments of the systems and computer readable media disclosed herein, the instructions further perform at least determining, by the computer, a geometric mean of w values of the target nucleotide sequence and/or the codon optimized nucleotide sequence.

In some embodiments of the systems and computer readable media disclosed herein, the target amino acid sequence corresponds to at least one protein (e.g., a therapeutic protein, a prophylactic protein, or the like). In some embodiments of the systems and computer readable media disclosed herein, the at least one problematic nucleotide sequence comprises at least 2, 3, 4, 5, 6, 7, 8, 9, 10, 11, 12, 13, 14, 15, 16, 17, 18, 19, 20, 30, 40, 50, 100, 500, or more problematic nucleotide sequences. In some embodiments of the systems and computer readable media disclosed herein, the at least one problematic nucleotide sequence corresponds to a splice site or a restriction enzyme recognition site. In some embodiments of the systems and computer readable media disclosed herein, the selected host expression system comprises a viral species, a fungal species, a bacterial species, or a mammalian species. In some embodiments of the systems and computer readable media disclosed herein, the selected codon table is a user specified codon table. In some embodiments of the systems and computer readable media disclosed herein, the selected codon table is automatically received when the selected host expression system is received.

In some embodiments of the systems and computer readable media disclosed herein, the plurality of candidate codon optimized nucleotide sequences comprises at least 100, 1000, 10000, 100000, or more nucleotide sequences. In some embodiments of the systems and computer readable media disclosed herein, a given candidate codon optimized nucleotide sequence in the plurality of candidate codon optimized nucleotide sequences comprises about 250 or fewer codons. In some embodiments of the systems and computer readable media disclosed herein, the synonymous codons each comprise a corresponding weight. In some embodiments of the systems and computer readable media disclosed herein, the corresponding weight is user specified.

In some embodiments of the systems and computer readable media disclosed herein, the instructions further perform at least replacing at least sub-sequences of any occurrences of the problematic nucleotide sequence in the codon optimized nucleotide sequence with unproblematic nucleotide sequences that do not alter the encoded target amino acid sequence to generate a further codon optimized nucleotide sequence. In some embodiments of the systems and computer readable media disclosed herein, the codon optimized nucleotide sequence comprises about 250 or more codons. In some embodiments of the systems and computer readable media disclosed herein, the instructions further perform at least identifying a start position of the problematic nucleotide sequence, a length of the problematic nucleotide sequence, and/or a number of problematic codons in the problematic nucleotide sequence at each occurrence of the problematic nucleotide sequence in the codon optimized nucleotide sequence to generate problematic nucleotide sequence data, and replacing at least the sub-sequences of any occurrences of the problematic nucleotide sequence in the codon optimized nucleotide sequence with the unproblematic nucleotide sequence that is randomly selected from a list of weighted unproblematic nucleotide sequences using the problematic nucleotide sequence data.

BRIEF DESCRIPTION OF THE DRAWINGS

The accompanying drawings, which are incorporated in and constitute a part of this specification, illustrate certain embodiments, and together with the written description, serve to explain certain principles of the methods, systems, and related computer readable media disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

DEFINITIONS

Figure 1A:
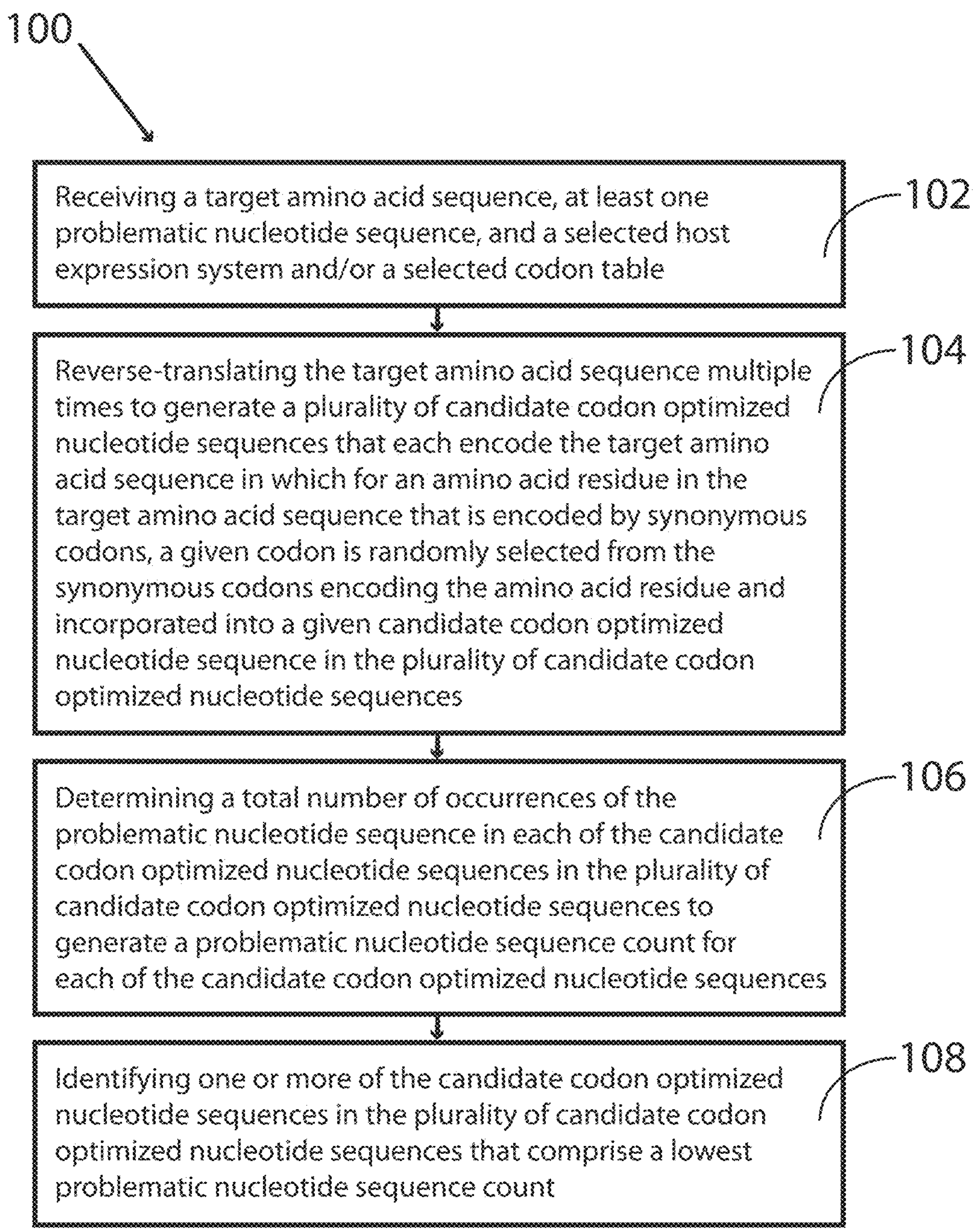
FIG. 1A is a flow chart that schematically shows exemplary method steps of generating a codon optimized nucleotide sequence using a computer according to some aspects disclosed herein.

In order for the present disclosure to be more readily understood, certain terms are first defined below. Additional definitions for the following terms and other terms may be set forth throughout the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains. In describing and claiming the methods, systems, and computer readable media, the following terminology, and grammatical variants thereof, will be used in accordance with the definitions set forth below.

About:

As used herein, "about" or "approximately" or "substantially" as applied to one or more values or elements of interest, refers to a value or element that is similar to a stated reference value or element. In certain embodiments, the term "about" or "approximately" or "substantially" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Codon:

As used herein, "codon" refers to a sequence of three nucleotides which together form a unit of genetic code in a DNA or RNA molecule that corresponds with a specific amino acid or stop signal during protein synthesis.

Codon Optimized Nucleotide Sequence:

As used herein, "codon optimized nucleotide sequence" refers to a progeny nucleotide sequence in which one or more codons have been changed relative to a parental nucleotide sequence such the progeny nucleotide sequence exhibits improved expression and/or another improved property relative to the parental nucleotide sequence when introduced into at least one host expression system.

Nucleic Acid:

As used herein, "nucleic acid" refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids can also include nucleotide analogs (e.g., bromodeoxyuridine (BrdU)), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA, cfDNA, ctDNA, or any combination thereof.

Sequence:

As used herein, ""sequence" in the context of a biopolymer refers to the order and identity of monomer units (e.g., nucleotides, amino acids, etc.) in the biopolymer or a representation of the biopolymer (e.g., a character string or the like). The sequence (e.g., base sequence) of a nucleic acid is typically read in the 5' to 3' direction.

Sub-sequence:

As used herein, ""sub-sequence" in the context of a biopolymer refers to any portion of the biopolymer's sequence.

Synonymous Codon:

As used herein, "synonymous codon" refers to a codon that encode the same amino acid as at least one other codon.

Protein:

As used herein, "protein" or "polypeptide" refers to a polymer of at least two amino acids attached to one another by a peptide bond. Examples of proteins include enzymes, hormones, antibodies, and fragments thereof.

DETAILED DESCRIPTION

The methods and related aspects of the present disclosure give users complete flexibility over designing the parameters used for the codon optimization of nucleotide sequences that encode amino acid sequences of interest. Unlike other codon optimization approaches, the host expression system used for the codon frequency table is not restricted to a select list of commonly used organisms. Instead, in some embodiments, the user can enter any organism that is listed on, for example, the NCBI.gov website to use the codon usage table that is on file. This ability is especially valuable for researchers and other users who work on rare or non-model organisms. In addition, for researchers and other users who have a specific or non-canonical codon usage needs, the methods and related aspects disclosed herein allow such users to upload custom codon tables with user-specified codon usage percentages. This further expands the flexibility of the methods and related aspects to meet user needs. Moreover, the methods and related aspects disclosed herein allow users to specify lists of splice sites, restriction enzyme recognition sites, or any other problematic nucleotide sequences that will be avoided during the automatic codon optimization.

These and other aspects will be apparent upon a complete review of the present disclosure, including the accompanying figures.

Figure 1B:
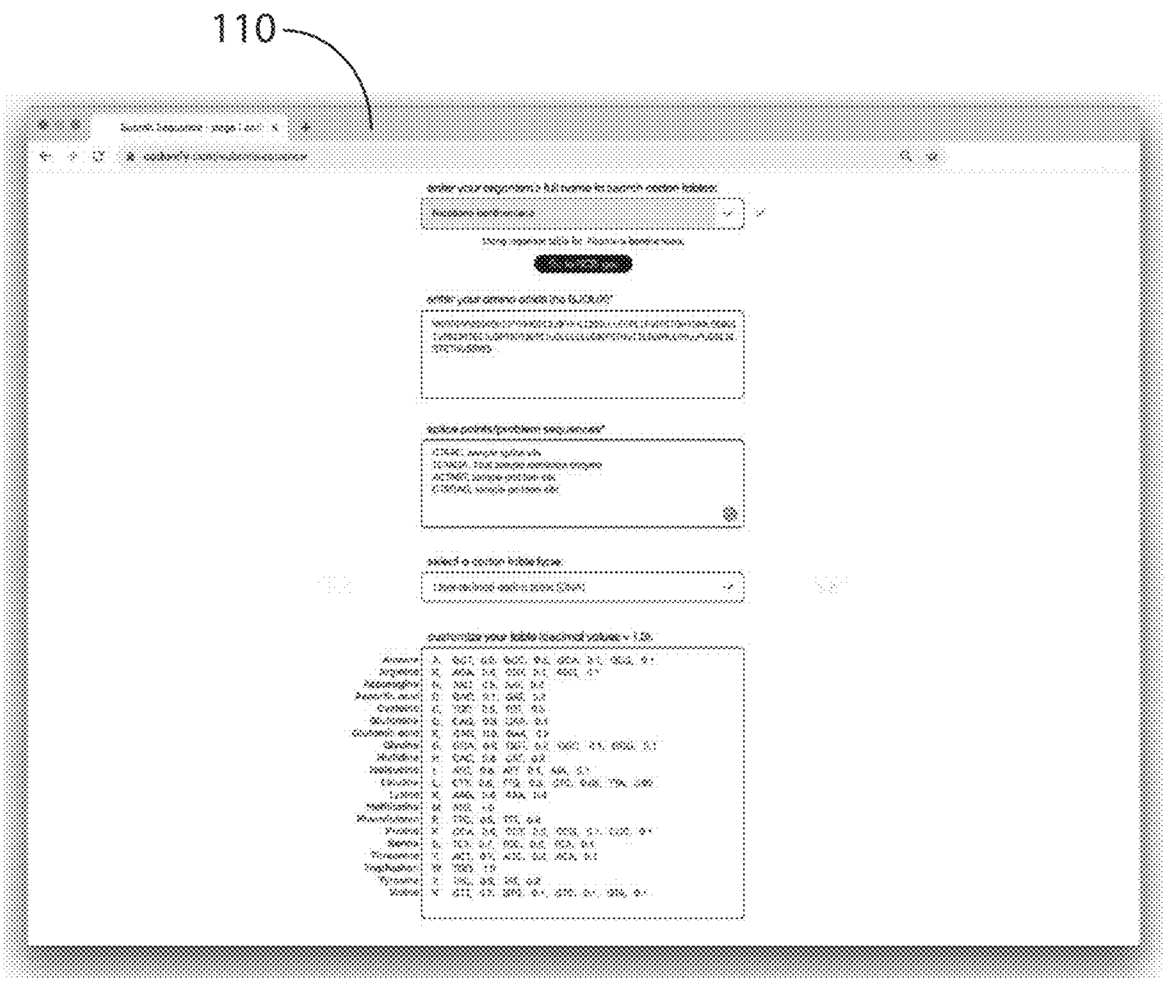
FIG. 1B is a screenshot of a user input page from a website according to some aspects disclosed herein.

To illustrate, FIG. 1A is a flow chart that schematically shows exemplary method steps of generating a codon optimized nucleotide sequence using a computer according to some embodiments. As shown, method 100 includes receiving, by the computer, a target amino acid sequence, at least one problematic nucleotide sequence, and a selected host expression system and/or a selected codon table (step 102). The target amino acid sequence generally corresponds to at least one protein (e.g., a pharmaceutically or prophylactically relevant protein, etc.). In some embodiments, a user inputs this information into the computer system via a website. For example, FIG. 1B is a screenshot of a user input page from a website according to some aspects disclosed herein. As shown, input page 110 allows users to select a desired host expression system, input the target amino acid sequence, designate problematic nucleotide sequence (e.g., splice sites, restriction enzyme recognition sites, and/or other sequences that may inhibit expression of nucleic acids by the selected host expression system), and select a user-defined codon table (e.g., with user-specified codon frequencies or the like). In some embodiments, users do not define a codon table as part of a given codon optimization process. In some of these embodiments, the computer system automatically obtains a codon table to be used from a storage unit of the system (e.g., a database or the like) or from a third-party repository or another source based upon the selected host expression system.

Method 100 also includes reverse-translating, by the computer, the target amino acid sequence multiple times to generate a plurality of candidate codon optimized nucleotide sequences that each encode the target amino acid sequence in which for an amino acid residue in the target amino acid sequence that is encoded by synonymous codons, a given codon is randomly selected from the synonymous codons encoding the amino acid residue and incorporated into a given candidate codon optimized nucleotide sequence in the plurality of candidate codon optimized nucleotide sequences (step 104). Method 100 also includes determining, by the computer, a total number of occurrences of the problematic nucleotide sequence in each of the candidate codon optimized nucleotide sequences in the plurality of candidate codon optimized nucleotide sequences to generate a problematic nucleotide sequence count for each of the candidate codon optimized nucleotide sequences (step 106). In addition, method 100 also includes identifying, by the computer, one or more of the candidate codon optimized nucleotide sequences in the plurality of candidate codon optimized nucleotide sequences that comprise a lowest problematic nucleotide sequence count (step 108).

Figure 1C:
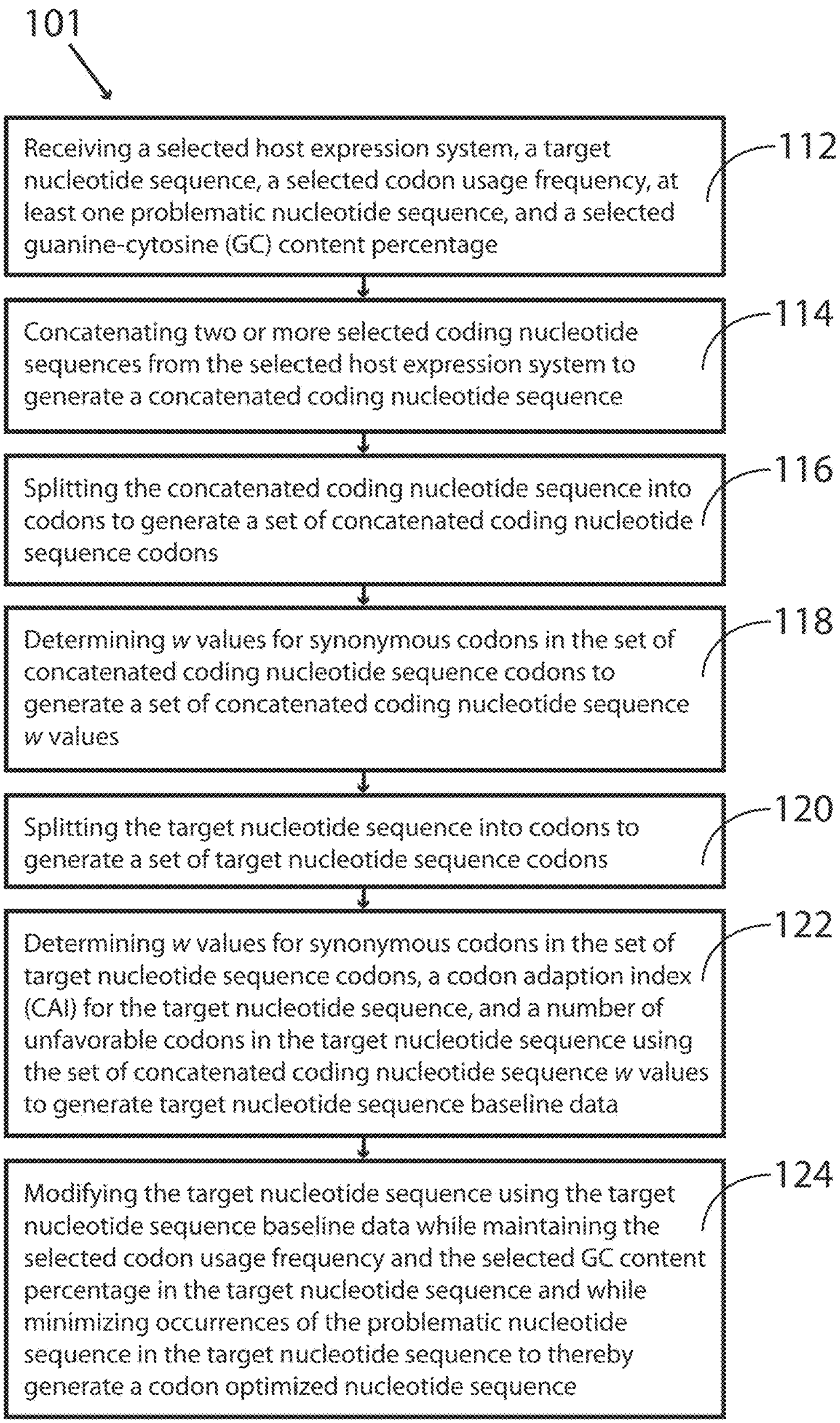
FIG. 1C is a flow chart that schematically shows exemplary method steps of generating a codon optimized nucleotide sequence using a computer according to some aspects disclosed herein.

To further illustrate, FIG. 1C is a flow chart that schematically shows other exemplary method steps of generating a codon optimized nucleotide sequence using a computer according to some aspects disclosed herein. As shown, method 101 includes receiving, by the computer, a selected host expression system, a target nucleotide sequence, a selected codon usage frequency, at least one problematic nucleotide sequence, and a selected guanine-cytosine (GC) content percentage (step 112). Typically, the target nucleotide sequence encodes at least one protein (e.g., a pharmaceutically or prophylactically relevant protein, etc.). Method 101 also includes concatenating, by the computer, two or more selected coding nucleotide sequences from the selected host expression system to generate a concatenated coding nucleotide sequence (step 114). Method 101 additionally includes splitting, by the computer, the concatenated coding nucleotide sequence into codons to generate a set of concatenated coding nucleotide sequence codons (step 116) and determining, by the computer, w values for synonymous codons in the set of concatenated coding nucleotide sequence codons to generate a set of concatenated coding nucleotide sequence w values (step 118).

In addition, method 101 also includes splitting, by the computer, the target nucleotide sequence into codons to generate a set of target nucleotide sequence codons (step 120) and determining, by the computer, w values for synonymous codons in the set of target nucleotide sequence codons, a codon adaption index (CAI) for the target nucleotide sequence, and a number of unfavorable codons in the target nucleotide sequence using the set of concatenated coding nucleotide sequence w values to generate target nucleotide sequence baseline data (step 122). Method 101 also includes modifying, by the computer, the target nucleotide sequence using the target nucleotide sequence baseline data while maintaining the selected codon usage frequency and the selected GC content percentage in the target nucleotide sequence and while minimizing occurrences of the problematic nucleotide sequence in the target nucleotide sequence to thereby generate a codon optimized nucleotide sequence (step 124). In some embodiments, method 101 includes determining a total number of codons, a number of unfavorable codons (e.g., synonymous codons that do not have the highest usage frequency in the expression system under consideration), a CAI, and/or a number of occurrences of the problematic nucleotide sequence in the codon optimized nucleotide sequence. In some embodiments, method 101 includes determining a geometric mean of w values of the target nucleotide sequence and/or the codon optimized nucleotide sequence.

In some embodiments of the methods disclosed herein, unfavorable or problematic nucleotide sequences correspond to splice sites, restriction enzyme recognition sites, and/or other nucleotide sequences that may inhibit expression of the nucleotide sequence in the selected host expression system. In some embodiments of the methods disclosed herein, for example, the problematic nucleotide sequence input by a user into the computer system includes at least 2, 3, 4, 5, 6, 7, 8, 9, 10, 11, 12, 13, 14, 15, 16, 17, 18, 19, 20, 30, 40, 50, 100, 500, or more problematic nucleotide sequences.

In some embodiments of the methods disclosed herein, the plurality of candidate codon optimized nucleotide sequences comprises at least 100, 1000, 10000, 100000, or more nucleotide sequences. In some embodiments of the methods disclosed herein, a given candidate codon optimized nucleotide sequence in the plurality of candidate codon optimized nucleotide sequences comprises about 250 or fewer codons. In some embodiments of the methods disclosed herein, the synonymous codons each comprise a corresponding weight. In some embodiments of the methods disclosed herein, the corresponding weight is user specified.

In some embodiments, the methods further include replacing, by the computer, at least sub-sequences of any occurrences of the problematic nucleotide sequence in the codon optimized nucleotide sequence with unproblematic nucleotide sequences that do not alter the encoded target amino acid sequence and that are less likely to inhibit expression of the codon optimized nucleotide sequence in the selected host expression system to generate a further codon optimized nucleotide sequence. In some embodiments of the methods disclosed herein, the codon optimized nucleotide sequence comprises about 250 or more codons.

In some embodiments of the methods disclosed herein, the method includes identifying, by the computer, a start position of the problematic nucleotide sequence, a length of the problematic nucleotide sequence, and/or a number of problematic codons in the problematic nucleotide sequence at each occurrence of the problematic nucleotide sequence in the codon optimized nucleotide sequence to generate problematic nucleotide sequence data. In these embodiments, the method also typically includes replacing, by the computer, at least the sub-sequences of any occurrences of the problematic nucleotide sequence in the codon optimized nucleotide sequence with the unproblematic nucleotide sequence that is randomly selected from a list of weighted unproblematic nucleotide sequences using the problematic nucleotide sequence data.

In some embodiments, the methods disclosed herein also include various post-sequence analysis steps for user-entered amino acid sequences and/or codon optimized nucleotide sequences. In the case of amino acid sequence analysis, for example, amino acid sequences are displayed in single-letter amino acid format with each letter hyperlinked in some embodiments. In some of these embodiments, when a user hovers over a given amino acid letter, a pop-up screen will appear to show an information panel for that amino acid. This panel typically includes the charge (positive, neutral, or negative), an image of the amino acid side chain structure, and/or other information about the particular amino acid. Optionally, this is done with hyperlinks and custom JavaScript and CSS. Optionally, hydrophobic and hydrophilic regions are highlighted in two different colors (e.g., red for hydrophobic regions and blue for hydrophilic regions in some embodiments). A matrix that is referenced to assign hydrophobicity or hydrophilicity or other information in some embodiments is shown in Table 1. In some embodiments, all cysteine (C) residues in a given amino acid sequence are marked to suggest potential sites for disulfide bands (e.g., HTML marking can be used to highlight cysteines).

grouped in sets of three for ease of reference. In some embodiments, AT or GC-rich regions are marked (e.g., regions in which more than seven out of 10 nucleotides or another proportion are AT or GC). In some of these embodiments, for example, color coded regions are used to allow users to see which areas of codon optimized nucleotide sequences are rich in certain types of nucleotides. In some embodiments, users are able to click any codon to see synonymous codons and to change those codons, if desired. If a new synonymous codon is selected, the new codon will replace the original codon in the sequence in some embodiments. This allows users to make manual edits to sequences to, for example, remove problematic nucleotide sequences or change AT/GC-rich regions. In some embodiments, these features are accomplished through a user interface on a website to permit the edits to the sequence before exporting the final sequence as a text file.

In some embodiments, the methods further include synthesizing a polynucleotide comprising the codon optimized nucleotide sequence or a further codon optimized nucleotide sequence encoding the target amino acid sequence. In some embodiments, the methods further include inserting the synthesized polynucleotide comprising the codon optimized nucleotide sequence encoding the target amino acid sequence into the selected host expression system (e.g., a viral species, a fungal species, a bacterial species, a mammalian species, an in vitro expression system, or the like), expressing a polypeptide that comprises the target amino acid sequence, and purifying the polypeptide.

The present disclosure also provides various systems and computer program products or machine readable media. In some aspects, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instruc-

TABLE 1

| Amino Acid | Code | Hydropathy | Charge | pKa, NH2 | pKa, COOH | pK(R) | Solubility |
|---|---|---|---|---|---|---|---|
| Arginine | R | hydrophilic | + | 9.09 | 2.18 | 13.2 | 71.8 |
| Asparagine | N | hydrophilic | N | 8.8 | 2.02 | | 2.4 |
| Aspartate | D | hydrophilic | − | 9.6 | 1.88 | 3.65 | 0.42 |
| Glutamate | E | hydrophilic | − | 9.67 | 2.19 | 4.25 | 0.72 |
| Glutamine | Q | hydrophilic | N | 9.13 | 2.17 | | 2.6 |
| Lysine | K | hydrophilic | + | 10.28 | 8.9 | 2.2 | |
| Serine | S | hydrophilic | N | 9.15 | 2.21 | | 36.2 |
| Threonine | T | hydrophilic | N | 9.12 | 2.15 | | freely |
| Cysteine | C | moderate | N | 10.78 | 1.71 | 8.33 | freely |
| Histidine | H | moderate | + | 8.97 | 1.78 | 6 | 4.19 |
| Methionine | M | moderate | N | 9.21 | 2.28 | | 5.14 |
| Alanine | A | hydrophobic | N | 9.87 | 2.35 | | 15.8 |
| Valine | V | hydrophobic | N | 9.72 | 2.29 | | 5.6 |
| Glycine | G | hydrophobic | N | 9.6 | 2.34 | | 22.5 |
| Isoleucine | I | hydrophobic | N | 9.76 | 2.32 | | 3.36 |
| Leucine | L | hydrophobic | N | 9.6 | 2.36 | | 2.37 |
| Phenylalanine | F | hydrophobic | N | 9.24 | 2.58 | | 2.7 |
| Proline | P | hydrophobic | N | 10.6 | 1.99 | | 1.54 |
| Tryptophan | W | hydrophobic | N | 9.39 | 2.38 | | 1.06 |
| Tyrosine | Y | hydrophobic | N | 9.11 | 2.2 | 10.1 | 0.038 |

Figure 2:
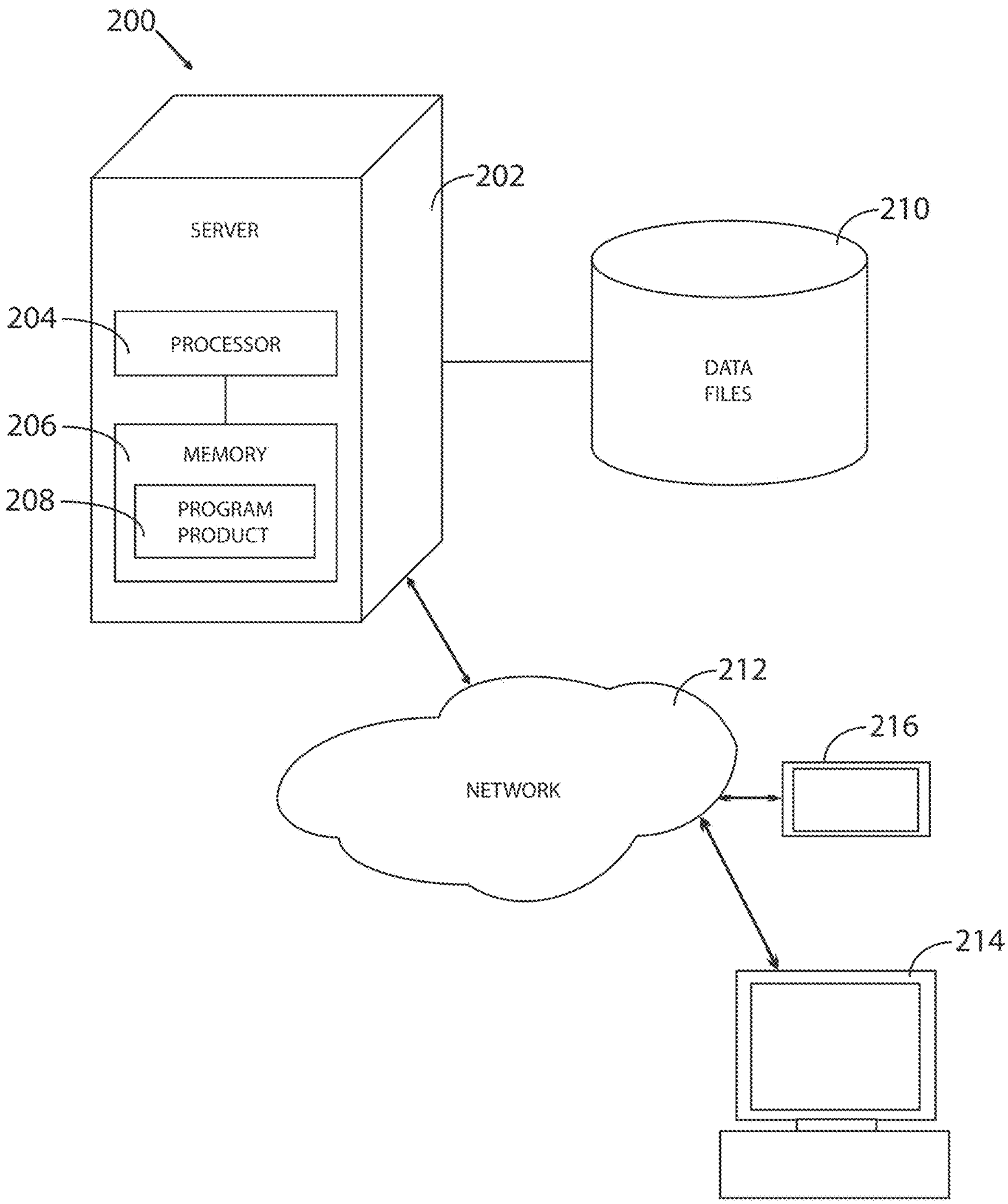
FIG. 2 is a schematic diagram of an exemplary system suitable for use with certain aspects disclosed herein.

In some embodiments, codon optimized nucleotide sequences are displayed with hyperlinked codons, for example, as part of additional nucleic acid sequence analysis steps. In some of these embodiments, any remaining problematic nucleotide sequences in a given optimized nucleotide sequence are highlighted. For example, using HTML, problematic nucleotide sequences can be highlighted and tions) and/or the like. To illustrate, FIG. 2 provides a schematic diagram of an exemplary system suitable for use with implementing at least aspects of the methods disclosed in this application. As shown, system 200 includes at least one controller or computer, e.g., server 202 (e.g., a search engine server), which includes processor 204 and memory, storage device, or memory component 206, and one or more other communication devices 214, 216, (e.g., client-side computer terminals, telephones, tablets, laptops, other mobile devices, etc. (e.g., for receiving codon optimized nucleotide sequences, etc.) in communication with the remote server 202, through electronic communication network 212, such as the Internet or other internetwork. Communication devices 214, 216 typically include an electronic display (e.g., an internet enabled computer or the like) in communication with, e.g., server 202 computer over network 212 in which the electronic display comprises a user interface (e.g., a graphical user interface (GUI), a web-based user interface, and/or the like) for displaying results upon implementing the methods described herein. In certain aspects, communication networks also encompass the physical transfer of data from one location to another, for example, using a hard drive, thumb drive, or other data storage mechanism. System 200 also includes program product 208 (e.g., for generating the codon optimized nucleotide sequences as described herein) stored on a computer or machine readable medium, such as, for example, one or more of various types of memory, such as memory 206 of server 202, that is readable by the server 202, to facilitate, for example, a guided search application or other executable by one or more other communication devices, such as 214 (schematically shown as a desktop or personal computer). In some aspects, system 200 optionally also includes at least one database server, such as, for example, server 210 associated with an online website having data stored thereon (e.g., entries corresponding to codon tables, host expression systems, nucleotide sequences, amino acid sequences, etc.) searchable either directly or through search engine server 202. System 200 optionally also includes one or more other servers positioned remotely from server 202, each of which are optionally associated with one or more database servers 210 located remotely or located local to each of the other servers. The other servers can beneficially provide service to geographically remote users and enhance geographically distributed operations.

As understood by those of ordinary skill in the art, memory 206 of the server 202 optionally includes volatile and/or nonvolatile memory including, for example, RAM, ROM, and magnetic or optical disks, among others. It is also understood by those of ordinary skill in the art that although illustrated as a single server, the illustrated configuration of server 202 is given only by way of example and that other types of servers or computers configured according to various other methodologies or architectures can also be used. Server 202 shown schematically in FIG. 2, represents a server or server cluster or server farm and is not limited to any individual physical server. The server site may be deployed as a server farm or server cluster managed by a server hosting provider. The number of servers and their architecture and configuration may be increased based on usage, demand and capacity requirements for the system 200. As also understood by those of ordinary skill in the art, other user communication devices 214, 216 in these aspects, for example, can be a laptop, desktop, tablet, personal digital assistant (PDA), cell phone, server, or other types of computers. As known and understood by those of ordinary skill in the art, network 212 can include an internet, intranet, a telecommunication network, an extranet, or world wide web of a plurality of computers/servers in communication with one or more other computers through a communication network, and/or portions of a local or other area network.

As further understood by those of ordinary skill in the art, exemplary program product or machine readable medium 208 is optionally in the form of microcode, programs, cloud computing format, routines, and/or symbolic languages that provide one or more sets of ordered operations that control the functioning of the hardware and direct its operation. Program product 208, according to an exemplary aspect, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 208 implementing the functionality or processes of various aspects of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 208 is optionally copied from the computer-readable medium to a hard disk or a similar intermediate storage medium. When program product 208, or portions thereof, are to be run, it is optionally loaded from their distribution medium, their intermediate storage medium, or the like into the execution memory of one or more computers, configuring the computer(s) to act in accordance with the functionality or method of various aspects disclosed herein. All such operations are well known to those of ordinary skill in the art of, for example, computer systems.

To further illustrate, in certain aspects, this application provides systems that include one or more processors, and one or more memory components in communication with the processor. The memory component typically includes one or more instructions that, when executed, cause the processor to provide information that causes at least one codon optimized nucleotide sequence and/or the like to be displayed (e.g., via communication devices 214, 216 or the like) and/or receive information from other system components and/or from a system user (e.g., via communication devices 214, 216, or the like).

In some aspects, program product 208 includes non-transitory computer-executable instructions which, when executed by electronic processor 204 perform at least: receiving a target amino acid sequence, at least one problematic nucleotide sequence, and a selected host expression system and/or a selected codon table. The instructions also perform reverse-translating the target amino acid sequence multiple times to generate a plurality of candidate codon optimized nucleotide sequences that each encode the target amino acid sequence, wherein for an amino acid residue in the target amino acid sequence that is encoded by synonymous codons, a given codon is randomly selected from the synonymous codons encoding the amino acid residue and incorporated into a given candidate codon optimized nucleotide sequence in the plurality of candidate codon optimized nucleotide sequences. The instructions also perform determining a total number of occurrences of the problematic nucleotide sequence in each of the candidate codon optimized nucleotide sequences in the plurality of candidate codon optimized nucleotide sequences to generate a problematic nucleotide sequence count for each of the candidate codon optimized nucleotide sequences. The instructions also perform identifying one or more of the candidate codon optimized nucleotide sequences in the plurality of candidate codon optimized nucleotide sequences that comprise a lowest problematic nucleotide sequence count to thereby generate a codon optimized nucleotide sequence. Other exemplary executable instructions that are optionally performed are described further herein.

EXAMPLES

Figure 3:
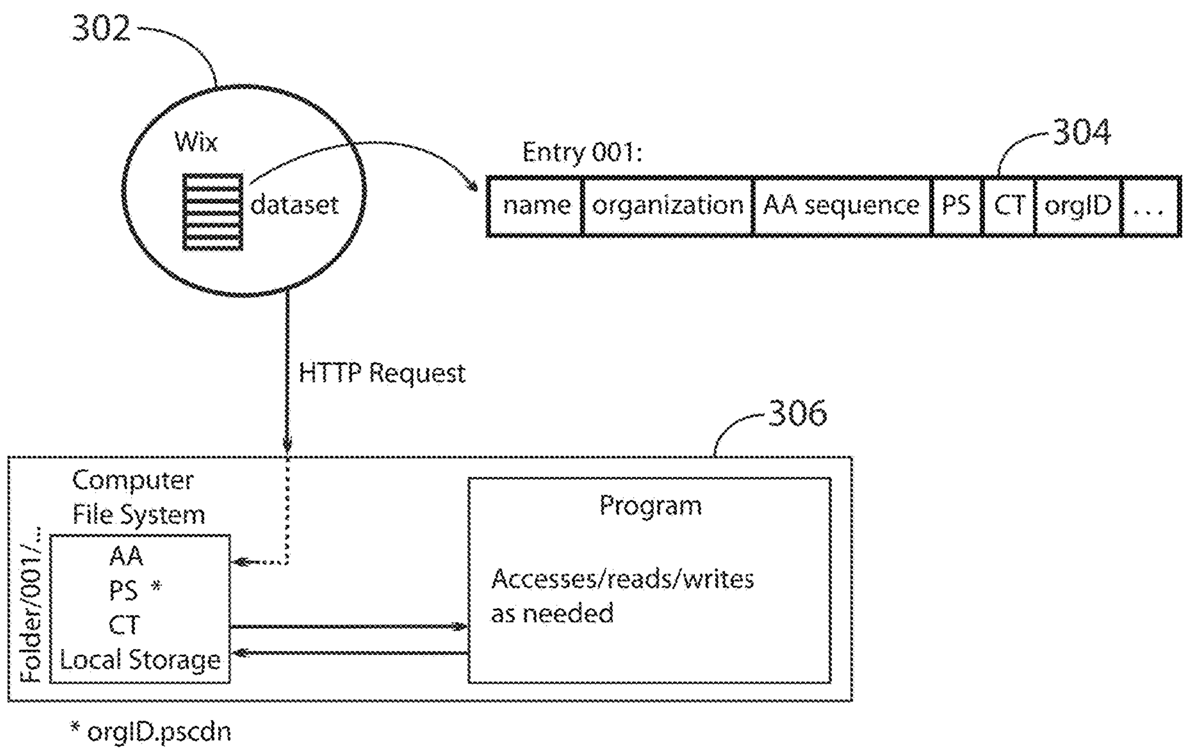
FIG. 3 is a flow chart that schematically shows the flow of information from a user to a dataset to a computer program product of the present disclosure according to some aspects disclosed herein.

Example 1: Embodiments of Brute Force and Auto Individual Replacement Codon Optimization Methods In this exemplary embodiment, the program takes in three main elements: an amino acid (AA) sequence, a list of problematic nucleotide sequences (PS), and a defined codon table (CT) with customized percentages. The AA and PS files is defined by the user, and the CT is optional. If no CT is given by the user, an NCBI organism ID is input, and the program automatically accesses a third-party source, such as kazusa.or.jp/codon/via the world wide web with the organism ID and pulls a tabulated codon table for use. An alert is sent to the administrator if suspicious organism IDs are given as an input. For example, an alert is sent for organism ID 9606: *Homo sapiens*. All data input is handled by the website codonify.com. Hosted by Wix, the website uses a custom form, datasets, and API requests via HTTP to access datasets. The submission form on the website is programmed to prompt the user to input the AA and PS submissions, while providing an option for the user to customize a codon table or input an organism ID. Submitting the program enters the data into a Wix dataset for retrieval by the program. The program is run on a personal computer and retrieves data when needed; capability for automatic pinging and dataset retrieval for 24/7 access can also be implemented. FIG. 3 is a flow chart that schematically shows the flow of information from a user to the dataset to the computer program product. As shown, user data entry 304 is included in dataset 302, which is then retrieved by program product 306.

Figure 4:
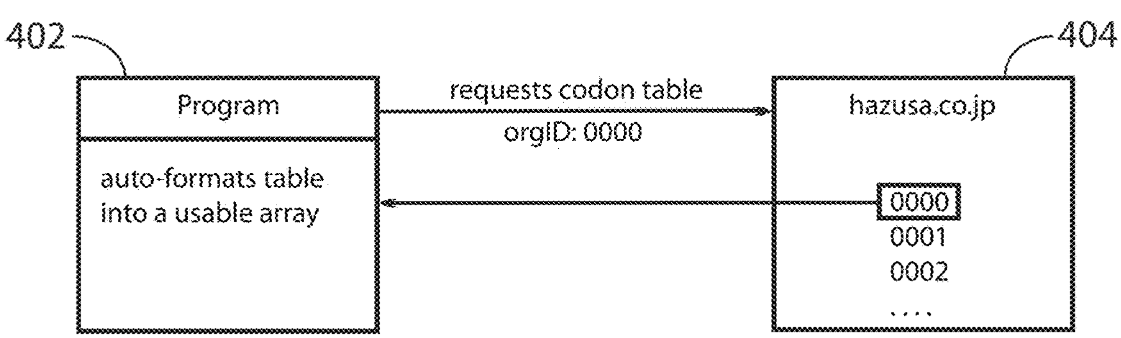
FIG. 4 schematically shows the conversion of a codon table obtained from an external source to an array that is suitable for use with a computer program product of the present disclosure according to some aspects disclosed herein.

After making an authorized HTTP request to Wix, the program downloads the most recent entry into files on local storage, reads the contents, and stores them into variables and arrays for later access. The AA sequence is a string, the PS list is converted into an array, and the CT is either directly accessed from the dataset if given, or a request to kasuza.or.jp/codon is made and the resulting data scraped, formatted, and tabulated into an array. To illustrate, FIG. 4 schematically shows the conversion of a codon table obtained from external source 404 to an array that is suitable for use with computer program product 402.

The conversion follows two paths: brute force for smaller sequences (see Illustrations below), and a find-and-replace sequence for longer sequences (see Illustrations below). For short sequences, the following happens: each amino acid is read, its related codon table entry is accessed, a random selection of a codon occurs with the defined weightings, and the codon is appended to a "result" string. This happens for each codon until a final sequence is generated. At this point, a search function runs and compares the entire string to each individual entry in the PS file. The total number of problems (i.e., problematic nucleotide sequences) are counted, stored, and an entirely new string is generated and compared again. This generation, comparison to PS, counting of problems, and regeneration happens up to 20,000 times. Each time a new string is randomly generated with a lower number of problems, it replaces the former best result and is stored.

After the randomized generation concludes, and if errors remain, or if there are more 250 codons, the auto individual replace stage commences. The program iterates through the potential result string in steps of 3 (since each codon is 3 characters long). It finds the start of a problem sequence, checks the length of the problem sequence, and finds the number of problematic codons. Then, it attempts to randomly (with the defined weights) find a new sub-sequence that can replace the problem site. Each attempt is again compared to the entire PS file to ensure that a new problem does not arise. This process happens continues down the list for each subsequence of problems. The sub-sequence comparison and replacement system provide a comprehensive capability to remove problem sequences, as computing power is redirected to only focus on sub-sequences of the potential result and not the entire sequence as a whole. After a complete traversal of the sequences for individual replacement, the resulting string is stored as a potential result, compared to the PS file, and if errors still exist, undergoes the individual replacement process again, up to 500 times as of now. If a new sequence is generated with fewer errors, the stored potential result is updated to the new sequence. If a result is generated with no errors, the loop breaks, and the program moves on to format the final sequence. After 500 attempts, the final sequence with the least errors is considered to be the final result and the program moves on to formatting. The program simply outputs a formatted sequence which is manually added to a PDF file and emailed to the user.

Illustrations:

Unless defined otherwise, the following will be the sample input:

AA:

MRMATPSSAPSVRNTEKRKN

CT:

G, GGA, 0.6, GGT, 0.2, GGC, 0.1, GGG, 0.1
P, CCA, 0.6, CCT, 0.2, CCG, 0.1, CCC, 0.1
A, OCT, 0.6, GCC, 0.2, GCA, 0.1, GCG, 0.1
V, GTT, 0.7, GTG, 0.1, GTC, 0.1, GTA, 0.1
L, CTT, 0.6, TTG, 0.3, CTC, 0.05, TTA, 0.05
I, ATC, 0.8, ATT, 0.1, ATA, 0.1
M, ATG, 1.0
C, TGC, 0.5, TGT, 0.5
F, TTC, 0.5, TTT, 0.5
Y, TAC, 0.8, TAT, 0.2
W, TGG, 1.0
H, CAC, 0.8, CAT, 0.2
K, AAG, 0.6, AAA, 0.4
R, AGA, 0.8, CGT, 0.1, AGG, 0.1
Q, CAG, 0.7, CAA, 0.3
N, AAC, 0.8, AAT, 0.2

E, GAG, 0.8, GAA, 0.2
D, GAC, 0.7, GAT, 0.3
S, TCT, 0.7, TCC, 0.2, TCA, 0.1
T, ACT, 0.7, ACC, 0.2, ACA, 0.1
PS:
GAGAAT, GCAGG, TTAGG, GTTAG, GTCAG
--------------------------------------------------------------------------------

Brute Force Method:
Iteration:
M (100% chance for ATG)→
R (80% chance for AGA, 10% chance of CGT, 108 for AGG)→
M (100% chance for ATG)→
A (60% chance for GCT, 20% chance for GCC, 10% chance for GCA, 10% chance for GCG)→
T, P, S, S, A, P, S, . . . , R, K, N
Random Result #1:
|M|R|M|A|T|P|S|S|A|P|S|V|R|N|T|E|K|R|K|N|
|ATG|AGA|ATG|GCC|ACT|C-CA|TCT|TCT|GCT|CCG|TCC|GT-T|AGA|AAT|ACC|GAG|AAG|AGG|AAA|AAC|
2 problem sequences found, retry #2 of 20000. [Underlined]
Random Result #2:
|M|R|M|A|T|P|S|S|A|P|S|V|R|N|T|E|K|R|K|N|
|ATG|CGT|ATG|GCG|ACT|CCG|TCT|TCC|GCT|CCT|TCT|GTT|AGA|AAC|ACT|GAG|AAA|AGA|AAG|AAC|
No problem sequences found.
Formatted Result:
|1|2|3|4|5|6|7|8|9|10|11|12|13|14|15|16|17|18|19|20|
|M|R|M|A|T|P|S|S|A|P|S|V|R|N|T|E|K|R|K|N|
|ATG|AGA|ATG|GCG|ACT|CCG|TCT|TCC|CCT|CCT|TCT|GTG|AGA|AAC|ACT|GAG|AAA|AGA|AAG|AAC|
--------------------------------------------------------------------------------

Auto Individual Replacement Method:
This happens if problems remain after 20 k random sequences (it will choose the best randomized sequence), or if the amino acids length is greater than 250 (it will generate a single random sequence and use that).
Initial Generation/Best Random Sequence:
|M|R|M|A|T|P|S|S|A|P|S|V|R|N|T|E|K|R|K|N|
|ATG|AGA|ATG|GCC|ACT|C-CA|TCT|TCT|GCT|CCG|TCC|GT-T|AGA|AAT|ACC|GAG|AAG|AGG|AAA|AAC|
2 problem sequences found. [Underlined]
Problem 1 starts at codon 1 (M), is of length 6, and ends in codon 3 (M).
Attempting replacement of M R M (using same codon table biases):
ATG AGA ATG --regenerate→ATG AGG ATG→Success!
Problem 2 starts at codon 12 (V), is of length 5, and ends in codon 13 (R).
Attempting replacement of V R (using same codon table biases):
GTT AGA --regenerate→CTC AGG --regenerate→GTC CGT→Success!
Insert and replace M R M and V R with new subsequences:
|M|R|M|A|T|P|S|S|A|P|S|V|R|N|T|E|K|R|K|N||ATG|AG-G|ATG|GCC|ACT|C-CA|TCT|TCT|GCT|CCG|TCC|GTC|CGT|AAT|ACC|GAG|AAG|AGG|AAA|AAC|
New sequence has no issues against PS list'
Formatted Result:
|1|2|3|4|5|6|7|8|9|10|11|12|13|14|15|16|17|18|19|20|
M|R|M|A|T|P|S|S|S|A|P|S|V|R|N|T|E|K|R|K|N|

|ATG|AGG|ATG|GCC|ACT|C-CA|TCT|TCT|GCT|CCG|TCC|GTC|CGT|AAT|ACC|GAG|AAG|AGG|AAA|AAC|
--------------------------------------------------------------------------------

Automatic Problem Sequence Finding Mechanism:
Say User 1 submits the following list of problems for organism 0001, an organism which has never been submitted before:
1. AATAAA
2. AATGGA
3. AATGAA
4. TATAAA
5. AATAAT
6. AATAAG A file is created 0001.pscdn and these problem sequences saved. The program runs and attempts to remove these six problems.
Say User 1 submits another sequence for organism 0001 with the following problem list:
1. AATAAA
2. AATGGA
3. AATGAA
4. TATAAA
5. AATAAT
6. AATAAG
7. AATATT
8. GATAAA (two new problems)

0001.pscdn is updated with the two new sequences.
The program runs and attempts to remove these eight problems.
Now User 2 submits a sequence for organism 0001 with the following problems:
1. AAAATA
2. ATTAAA
3. AATTAA
4. AATACA
5. CATAAA
6. ACTAAA When the program is run, it will attempt to remove 14 problems:
1. AAAATA
2. ATTAAA
3. AATTAA
4. AATACA
5. CATAAA
6. ACTAAA (User 2-defined problems)
7. AATAAA
8. AATGGA
9. AATGAA
10. TATAAA
11. AATAAT
12. AATAAG
13. AATATT
14. GATAAA (known problem sequences from before)

This element of the program allows users to receive sequences that are potentially optimized beyond their problem sequences, since our database of problems can consistently grow with usage and provide more intelligent sequences even when few problems are defined by the user.

Example 2: Embodiments of Concatenation-Based Codon Optimization Methods

Introduction

Codon usage bias arises because organisms do not randomly employ synonymous codons (codons that specify the same amino acid. Of the twenty standard amino acids, three have six synonymous codons, five have four synonymous codons, one has three, nine have two and there are only two amino acids encoded by single codon each). Instead, some organisms preferentially use some synonymous codons more than others.

Moreover, proteins present at high levels within cells are often encoded by genes that have a codon usage bias common among those highly translated proteins. This bias typically differs considerably among various organisms.

The codon usage bias can also be employed strategically by the cell to slow down the translation process in certain regions of the mRNA (corresponding the coding region of a gene), presumably to allow the section of the protein already protruding out of the ribosome to fold properly before the protein can be extended further To allow for quantitative comparisons of the codon bias between genes and gene regions, a well-accepted metric such as the Codon Adaptiveness Index (CAI) can be used. The relative synonymous codon usage (RSCU) of each codon within a reference group (e.g., a group of genes whose translated products are highly expressed) is calculated by dividing the actual frequency of a codon within the pool by the expected frequency if no bias is assumed. The RSCU values are then normalized for the highest value within the codons for each amino acid to obtain the w value. CAI is the geometric mean of the w values across the length of the DNA coding sequence of a particular protein. Localized CAI can be also calculated for different parts of the coding region.

A DNA sequence employing more preferred codons (higher w values) will have a higher CAI. The CAI of the pool of highly translated proteins is usually around 0.8. The goal of the optimization process is to adapt a foreign sequence to bring its CAI value close to 0.8.

Step 1: Obtaining w Values

A. Name of organism that will be used for expression

B. cDNA sequences of highly expressed proteins in the desired expression organism (ex. *E. coli*): The user will input the name of the expression organism into a text entry box. After obtaining the organism name, the relevant proteomic database will be referenced to find the top 10 most highly expressed native proteins and the cDNA sequences for these proteins obtained. If the proteome for the desired organism is not available, options for current proteomic databases will be provided. A list of the protein names will be presented to the user and will provide the user with the choice to:

1) accept the protein choices for the next steps of the analysis
2) remove one or more of the protein choices
3) replace the presented choices with a user specified protein Alternatively, users will be allowed to enter the NCBI IDs for up to ten proteins that will be used for the codon usage analysis.

C. DNA sequence to be optimized

Internal Process:

1. Take cDNA sequences from all 10 proteins, combine them end-to-end into a single final sequence, split them into codons (groups of three characters),
   a. Done with arrays and list structures
2. Group them based on the amino acid that they encode (ex. TTT and TTC both encode Phe).
   a. Done with arrays and list structures
3. Count how many times each codon is repeated in the sequence (ex. how many times TTT appears as a codon in the final sequence, repeat for the remaining 63 potential codons). Find the following percentages:
   a. The percentage describing the usage of each codon based on the total number of codons (ex. output: TTT comprises 1.51% of the total codons). Repeat for all the other codons that encode a particular amino acid (ex. both TTT and TTC encode for Phe. TTT comprises 1.51% of the total codons and TTC comprises 3.68% of the total codons).
   b. For each amino acid, sum the percentage values obtained in 3a (ex. 1.51+3.68=5.19).
   c. Find the relative usage for each codon that encodes the same amino acid (ex. based on the reference pool specified in step 1, for all instances of the amino acid Phe, TTT is used 29% of the time while TTC is used 71% of the time. Convert to decimals so that the sum of the values equals 1 [TTT=0.29 and TTC=0.71]).
   d. Find the relative synonymous codon usage (RSCU) by dividing the percentage of each codon occurrence by the number of potential codons that encode for a certain protein (ex: the observed frequency of TTT is 0.29 and there are two codons that encode Phe so the RSCU is 0.29/2 or 0.581). Repeat for the other synonymous codons.
   e. Find w by normalizing the values in id above by setting the highest value for a synonymous codon to 1.
   f. Mark all codons that have a relative usage score from 1c less than or equal to 0.5 as 'unfavorable'.
   g. This is accomplished programmatically with string search and index find functions within loops to iterate through the length of the sequence, storing the data as it is found in multidimensional arrays. Each sum is accomplished via customized functions designed to recreate the above math.

TABLE 1

| | | abundant | | Nicotiana benthamiana | | | | | | |
|---|---|---|---|---|---|---|---|---|---|---|
| | | % of Total codons | % of AA codons | % of Total codons | % of AA codons | Number of codons E | Number of codons O | Number of codons (O-E)^2/E | RSCU | w |
| Phe | UUU | 1.51 | 0.29 | 2.19 | 0.51 | 383932.27 | 678320.00 | 225727.67 | 0.581 | 0.410 |
| | UUC | 3.68 | 0.71 | 2.07 | 0.49 | 926794.73 | 642407.00 | 92511.34 | 1.439 | 1.000 |
| | 2 | 5.19 | 1.00 | 4.26 | 1.00 | 1320727.00 | 1320727.00 | 318239.01 | | |

4. Convert the user input DNA sequence into codons and apply the w values for each codon based on the w values derived in 3e. This is the baseline value before optimization has occurred.
   a. This sequence is based on the 10 proteins originally given and stored for future use and future dataset training.
5. Find the geometric mean of the w value for each codon (n) with the range of n−9 to n+9.
   a. This uses the w-values to generate a tabulated dataset for the end user for each codon. For ease-of-use, a function will be written that performs this role using array manipulation.
6. Obtain the codon adaption index (CAI) by finding the geometric mean of the w values.
   a. Another dataset will be generated upon those w-values and a CAI value appended to the final report for the end user. Another snippet of code will iterate through the w-value array and produce the CAI value. For each production of a data element, it will be appended to the final file to be sent to the user, ensuring that little to no human interaction is needed to download a sequence from the Website dataset, perform these operations, and submit the resulting data back.

Output

1. Table containing the amino acids, the synonymous codons encoding each amino acid, and the w value for each codon (see Internal Process 3e).
2. Graph containing the values of Internal process 5.
3. Table containing the names of the protein cDNA sequences used in Input 1, the CAI for the user-entered sequence, and the number of unfavorable codons (codons with a w value less than or equal to 0.5).

Step 2: Optimizing the User-Entered Sequence

Prefilled Inputs

1. DNA sequence from STEP 1
2. Codon table with marked unfavorable codons

User Inputs

1. Codon usage frequency
2. Problem nucleotide sequences to avoid
3. Ideal percentage of GC-rich regions (offer range from 35-65%)

Internal Processes

1. Take the DNA sequence and optimize it to remove the problem sequences while maintaining the user-entered codon usage frequencies.
   a. This will be done with the usage of TensorFlow and other machine learning algorithms, retraining the dataset with each new submission. Combined with the historical problem sets from other submissions of the same organism, along with the given codon table weighting biases, an intelligently optimized sequence can be generated with a high level of accuracy. Leveraging cloud services like Microsoft Azure will increase the compute time, decreasing the time from input to result for the end user.
2. Maintain GC-percentage
   a. Using the given GC percentage when training the dataset for a sequence generation will help to produce a result that is within a few percent of the desired range. Post-processing analysis will assist with specific codon replacements if needed.
3. Add the w values for each codon based on the w values derived in STEP 1.
   a. Generate an additional w plot graph with the newly optimized sequence.
4. Find the geometric mean of the w value for each codon (n) with the range of n−9 to n+9.
   a. Using the same function from Step 1, another tabulated dataset is generated for the w-values for each codon
5. CAI value for optimized sequence (same procedure as in STEP 1)
   a. Using the above dataset, a CAI value is generated for the optimized sequence. For each production of a data element, it will be appended to the final file to be sent to the user, ensuring that little to no human interaction is needed to download a sequence from the Website dataset, perform these operations, and submit the resulting data back.

User Outputs

1. Codon-optimized sequence
2. Display table comparing the following values between the unoptimized and optimized sequences
   a. Number of total codons
   b. Number of unfavorable codons
   c. CAI value
   d. Number of problem sequences
3. Une graph comparing the geographical means of the w values of the unoptimized and optimized sequences (STEP 1 Internal Process 5 vs STEP 2 Internal Process 4). Mark the CAI value of each sequence as a dotted line across the graph.

Request the user to accept the sequence and log out of the session.

In some embodiments, the program can be expanded to permit predictions for the problematic nucleotide sequences based on past user entries with large datasets. In some embodiments, post-submission forms are provided for users to indicate whether the codon optimized nucleotide sequence worked and if so, a percentage improvement value. These post-submission forms can be used as input to the datasets to produce a more viable result for subsequent users of the same host expression system.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, and/or computer readable media or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A method of synthesizing a polynucleotide using a computer, the method comprising:

receiving, by the computer, a target amino acid sequence, at least one problematic nucleotide sequence, and a selected host expression system and/or a selected codon table, wherein the problematic nucleotide sequence comprises a guanine-cytosine content (GC content), a sequence repeat, a splice site, and/or a restriction enzyme recognition site that negatively affects transcription and/or translation in the selected host expression system;

reverse-translating, by the computer, the target amino acid sequence multiple times to generate a plurality of candidate codon optimized nucleotide sequences that each encode the target amino acid sequence, wherein a given candidate codon optimized nucleotide sequence in the plurality of candidate codon optimized nucleotide sequences comprises about 250 or fewer codons, wherein the plurality of candidate codon optimized nucleotide sequences comprises at least 100, 1000, 10000, 100000, or more nucleotide sequences, and wherein for an amino acid residue in the target amino acid sequence that is encoded by synonymous codons, a given codon is randomly selected from the synonymous codons encoding the amino acid residue and incorporated into a given candidate codon optimized nucleotide sequence in the plurality of candidate codon optimized nucleotide sequences;

determining, by the computer, a total number of occurrences of the problematic nucleotide sequence in each of the candidate codon optimized nucleotide sequences in the plurality of candidate codon optimized nucleotide sequences to generate a problematic nucleotide sequence count for each of the candidate codon optimized nucleotide sequences;

identifying, by the computer, one or more of the candidate codon optimized nucleotide sequences in the plurality of candidate codon optimized nucleotide sequences that comprise a lowest problematic nucleotide sequence count, thereby generating the codon optimized nucleotide sequence;

identifying, by the computer, a start position of the problematic nucleotide sequence, a length of the problematic nucleotide sequence, and/or a number of problematic codons in the problematic nucleotide sequence at each occurrence of the problematic nucleotide sequence in the codon optimized nucleotide sequence to generate problematic nucleotide sequence data;

replacing, by the computer, at least a sub-sequences of any occurrences of the problematic nucleotide sequence in the codon optimized nucleotide sequence with an unproblematic nucleotide sequence that is randomly selected from a list of weighted unproblematic nucleotide sequences using the problematic nucleotide sequence data, thereby generating a further codon optimized nucleotide sequence, wherein the unproblematic nucleotide sequence does not negatively affect transcription and/or translation in the selected host expression system; and, synthesizing a polynucleotide comprising the further codon optimized nucleotide sequence encoding the target amino acid sequence.

2. The method of claim 1, further comprising:

determining, by the computer, a total number of codons, a number of unfavorable codons, a CAI, and/or a number of occurrences of the problematic nucleotide sequence in the codon optimized nucleotide sequence.

3. The method of claim 1, wherein the target amino acid sequence corresponds to at least one protein.

4. The method of claim 1, wherein the at least one problematic nucleotide sequence comprises at least 2, 3, 4, 5, 6, 7, 8, 9, 10, 11, 12, 13, 14, 15, 16, 17, 18, 19, 20, 30, 40, 50, 100, 500, or more problematic nucleotide sequences.

5. The method of claim 1, wherein the at least one problematic nucleotide sequence corresponds to a splice site or a restriction enzyme recognition site.

6. The method of claim 1, wherein the selected host expression system comprises a viral species, a fungal species, a bacterial species, or a mammalian species.

7. The method of claim 1, wherein the selected codon table is a user specified codon table.

8. The method of claim 1, wherein the selected codon table is automatically received when the selected host expression system is received by the computer.

9. The method of claim 1, wherein the synonymous codons each comprise a corresponding weight.

10. The method of claim 9, wherein the corresponding weight is user specified.

11. The method of claim 1, wherein the codon optimized nucleotide sequence comprises about 250 or more codons.

12. The method of claim 1, further comprising:

inserting the synthesized polynucleotide comprising the further codon optimized nucleotide sequence encoding the target amino acid sequence into the selected host expression system;

expressing a polypeptide that comprises the target amino acid sequence; and, purifying the polypeptide.

13. A method of synthesizing a polynucleotide using a computer, the method comprising:

receiving, by the computer, a target amino acid sequence, at least one problematic nucleotide sequence, and a selected host expression system and/or a selected codon table, wherein the at least one problematic nucleotide sequence corresponds to a splice site or a restriction enzyme recognition site that negatively affects transcription and/or translation in the selected host expression system;

reverse-translating, by the computer, the target amino acid sequence multiple times to generate a plurality of candidate codon optimized nucleotide sequences that each encode the target amino acid sequence, wherein the plurality of candidate codon optimized nucleotide sequences comprises at least 100, 1000, 10000, 100000, or more nucleotide sequences, and wherein for an amino acid residue in the target amino acid sequence that is encoded by synonymous codons, a given codon is randomly selected from the synonymous codons encoding the amino acid residue and incorporated into a given candidate codon optimized nucleotide sequence in the plurality of candidate codon optimized nucleotide sequences;

determining, by the computer, a total number of occurrences of the problematic nucleotide sequence in each of the candidate codon optimized nucleotide sequences in the plurality of candidate codon optimized nucleotide sequences to generate a problematic nucleotide sequence count for each of the candidate codon optimized nucleotide sequences;

identifying, by the computer, one or more of the candidate codon optimized nucleotide sequences in the plurality of candidate codon optimized nucleotide sequences that comprise a lowest problematic nucleotide sequence count, thereby generating the codon optimized nucleotide sequence;

identifying, by the computer, a start position of the problematic nucleotide sequence, a length of the problematic nucleotide sequence, and/or a number of problematic codons in the problematic nucleotide sequence at each occurrence of the problematic nucleotide sequence in the codon optimized nucleotide sequence to generate problematic nucleotide sequence data;

replacing, by the computer, at least a sub-sequences of any occurrences of the problematic nucleotide sequence in the codon optimized nucleotide sequence with an unproblematic nucleotide sequence that is randomly selected from a list of weighted unproblematic nucleotide sequences using the problematic nucleotide sequence data, thereby generating a further codon optimized nucleotide sequence, wherein the unproblematic nucleotide sequence does not negatively affect transcription and/or translation in the selected host expression system; and, synthesizing a polynucleotide comprising the further codon optimized nucleotide sequence encoding the target amino acid sequence.

* * * * *